US005959129A

United States Patent [19]

van Dam et al.

[11] Patent Number: 5,959,129

[45] Date of Patent: Sep. 28, 1999

[54] FRACTIONATION OF TRIGLYCERIDE OILS

[75] Inventors: Petrus Henricus J van Dam, Rotterdam; Wim Hogervorst; Frans Kamp, both of Spijkenisse, all of Netherlands

[73] Assignee: Unilever Patent Holdings B.V., Vlaardingen, Netherlands

[21] Appl. No.: 08/930,493

[22] PCT Filed: Mar. 21, 1996

[86] PCT No.: PCT/EP96/01241

§ 371 Date: Oct. 3, 1997

§ 102(e) Date: Oct. 3, 1997

[87] PCT Pub. No.: WO96/31580

PCT Pub. Date: Oct. 10, 1996

[30] Foreign Application Priority Data

| | | | |
|---|---|---|---|
| Apr. 5, 1995 | [EP] | European Pat. Off. | 95200858 |
| Dec. 21, 1995 | [EP] | European Pat. Off. | 95203598 |

[51] Int. Cl.$^6$ .......... C07C 59/00

[52] U.S. Cl. .......... 554/215; 554/211; 426/417

[58] Field of Search .......... 554/211, 215; 426/417

[56] References Cited

U.S. PATENT DOCUMENTS

| | | | |
|---|---|---|---|
| 3,059,009 | 10/1962 | Schmid et al. | 260/428 |

FOREIGN PATENT DOCUMENTS

| | | | |
|---|---|---|---|
| 2 208 466 | 4/1989 | United Kingdom . | |
| WO 95/04123 | 2/1995 | WIPO | C11B 7/00 |

OTHER PUBLICATIONS

Yuki et al, J. Jpn. Oil Chem. Soc., 39(4):236–244 (1990).

Derwent Publications Ltd., Abstract AN 94–251621 (Jul. 5, 1994).

Derwent Publications Ltd., Abstract AN 93–200723 (May 21, 1993).

*Primary Examiner*—Gary Geist
*Assistant Examiner*—Deborah D Carr
*Attorney, Agent, or Firm*—Pillsbury Madison & Sutro, LLP

[57] ABSTRACT

Fractionation of lauric oils which contain a crystallization modifying substance consisting of a sucrose ester containing at least 40 wt. % laurate. With palmkernel oil fractionation a separation efficiency of more than 70% can be attained.

8 Claims, 1 Drawing Sheet

FRACTIONATION OF TRIGLYCERIDE OILS

This application is the national phase of international application PCT/EP96/01241, filed Mar. 21, 1996 which was designated the U.S.

The present invention is concerned with a process for fractionating triglyceride oils, particularly lauric oils. The fractionation (fractional crystallization) of triglyceride oils is described by Gunstone, Harwood and Padley in The Lipid Handbook, 1986 edition, pages 213–215. Generally triglyceride oils are mixtures of various triglycerides having different melting points. Lauric oils are triglyceride oils which contain a considerable amount of esterified lauric acid, such as coconut oil (CN), palmkernel oil (PK) and derivatives thereof. The composition of triglyceride oils may be modified e.g. by fractionation yielding a fraction having a different melting point or solubility.

One fractionation method is the so-called dry fractionation process which comprises cooling the oil until a solid phase crystallises and separating the crystallised phase from the liquid phase. The liquid phase is denoted as olein fraction, while the solid phase is denoted as stearin fraction.

The separation of the phases is usually carried out by filtration, optionally applying some kind of pressure.

The major problem encountered with phase separation in the dry fractionation process is the inclusion of a lot of liquid olein fraction in the separated stearin fraction. The olein fraction is thereby included in the inter- and intracrystal spaces of the crystal mass of the stearin fraction. Therefore the separation of the solid from the liquid fraction is only partial.

The solids content of the stearin fraction is denoted as the separation efficiency. In dry fractionation it seldom surpasses 50 to 60 wt. %. This is detrimental to the quality of the stearin as well as to the yield of the olein. For the related solvent fractionation process, where the fat to be fractionated is crystallised from e.g. a hexane or acetone solution, separation efficiencies may be up to 95%.

Dry fractionation, however, is a process which is more economical and more environmentally friendly than solvent fractionation. For dry fractionation an increase of separation efficiency is therefore much desired, particularly for the commercially very important lauric oils.

It is known to interfere with the crystallization by adding to a crystallising oil a substance which will generally be indicated as a crystallization modifying substance. The presence of small quantities of such a substance in the cooling oil may accelerate, retard or inhibit crystallization. In certain situations the above substances are more precisely indicated as crystal habit modifiers. Known crystallization modifiers are e.g. fatty acid esters of sucrose, described in U.S. Pat. Nos. 3,059,010, 3,059,010, JP 05/125389 and JP 06/181686, fatty acid esters of glucose and derivatives, described in U.S. Pat. No. 3,059,011. These crystallization modifiers are effective in speeding up the crystallization rate.

Other crystallization modifiers, e.g. as described in U.S. Pat. No. 3,158,490 when added to kitchen oils have the effect that solid fat crystallization is prevented or at least retarded. Other types of crystallization modifiers, particularly referred to as crystal habit modifiers, are widely used as an ingredient for mineral fuel oils in which waxes are prone to crystallize at low temperatures. U.S. Pat. No. 3,536,461 teaches the addition of a crystal habit modifier to fuel oil with the effect that the cloud point (or pour point) temperature is lowered far enough to prevent crystal precipitation. Or, alternatively, the solids are induced to crystallize in a different habit so that the crystals when formed can pass fuel filters without clogging them. Other crystal habit modifiers are actually able to change the habit of the crystallized triglyceride fat crystals in a way such that after crystallization the crystals, the stearin phase, can be more effectively separated from the liquid phase, the olein phase. Publications describing such crystal habit modifiers are e.g. GB 1 015 354, U.S. Pat. No. 2,610,915, co-pending PCT application WO 95/04122, U.S. Pat. Nos. 3,059,008, 3,059,009 and 3,059,010.

Separation efficiency also depends on the mode of crystallisation, either stagnant or stirred. Often good results are obtained with stagnant crystallisation rather than with stirred crystallisation. From the point of view of process economy, however, stirred crystallization is preferred.

Lauric oils often crystallize in a needle-like morphology. The resulting crystal agglomerates (see FIG. 1A) easily include olein. Fractionation by stirred crystallization is sometimes impossible because the hydrodynamic shear would crush the needles and produces crystal slurries which often can be hardly or not separated in a stearin and an olein hase. Palmkernel oil fractionation is not possible except in a stagnant mode and therefore is a very labour intensive process. For lauric oils an effective separation efficiency enhancing substance is badly needed.

STATEMENT OF INVENTION

It has been found that the presence of a sucrose laurate in the fractionation of lauric oils causes crystallization of large and non-porous spherulites which highly increases the separation efficiency. Accordingly the invention relates to a process for separating solid fatty material crystallised from lauric oils, which comprises the steps:

a. heating the oil until no longer a substantial amount of solid triglyceride is present in the oil, b. cooling and crystallising the triglyceride oil resulting in a solid stearin phase besides a liquid olein phase and c. recovering the stearin phase by separating it from the olein phase, where before crystallization starts a crystallization modifying substance is added to said triglyceride oil or to a solution of said triglyceride oil in an inert solvent, characterized in that the crystallization modifying substance is a sucrose laurate.

DETAILS OF THE INVENTION

Figure 1A:
FIG. 1A shows agglomerates of needle-like crystals of palmkernel oil obtained by quiescent crystallization without additive.

The lauric oil to be fractionated is mixed with the crystallization modifying substance (the additive) before crystallization starts, preferably before the oil is heated or dissolved in the solvent so that all solid triglyceride fat and preferably also the modifying substance is liquefied.

The lauric oil can be any triglyceride oil or a mixture of triglyceride oils having a content of lauric acid which is 10–75 wt. %, preferably 20–60 wt. %, more preferably 30–60 wt. % calculated on total fatty acid content, for example coconut oil or palmkernel oil. The oils may have been prepared with the use of fractionation, hydrogenation or (chemical or enzymatic) interesterification.

Sucrose laurate in the context of this description denotes a sucrose ester of which on average at least four, preferably five to six of the eight hydroxyl groups have been esterified with a fatty acid. 40–100 wt. %, preferably 60–100 wt. %, more preferably 75–100 wt. % of the fatty acids should be lauric acid. The ester can be obtained by well-known usual processes such as esterification of sucrose with a lauric acid containing mixture of fatty acids or of reactive fatty acid derivatives. Sucrose with more than four free hydroxyl groups has an insufficient oil solubility. Sucrose polylaurate as mentioned in this specification is a highly esterified (50–100%) sucrose ester with a lauric-content of 95 wt. %. It is a readily available commercial product (e.g. Ryoto Sugar Ester L195, ex MITSUBISHI).

When the mixture of triglyceride and sucrose laurate has been liquefied, the oil or solution is cooled to the chosen crystallization temperature. A suitable temperature range is 15–35° C. To each temperature belongs a specific composition of the olein and stearin phases. Crystallization proceeds at the chosen temperature until the crystallised oil stabilises to a constant solid phase content. The crystallization time increases when more solid phase is desired and the temperature is lowered. Usual times are in the range of 4–16 hours. During crystallization the oil may remain quiescent or is stirred, e.g. with a gate stirrer. Sucrose laurate is effective in stirred crystallization as well as in quiescent crystallization.

The stearin and olein phases may be separated by filtration but for an effective separation of the solid from the liquid phase the higher pressures of a membrane filter press are used. Suitable pressures are 3–50 bar, exerted for about 20–200 minutes. However, the invention allows a low or moderate pressure. As a rule with a pressure of 6–12 bar it takes about 30–60 minutes to get a proper separation of the stearin phase from the olein phase.

The solids content of the crystal slurry before separation and of the stearin phase obtained after separation is measured according to the known pulse NMR method (ref. Fette, Seifen, Anstrichmittel 1978, 80, nr. 5, pp. 180–186).

The effect of the invention is believed to be caused by alteration of the crystal structure or crystal habit of the stearin under the influence of the additive. These might interfere in different ways with the growth of the various crystal faces.

Figure 1B:
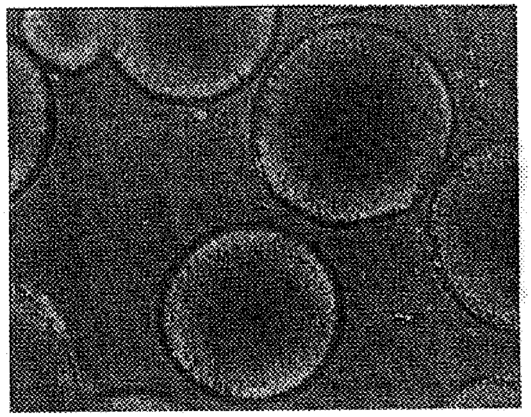
FIG. 1B shows spherulite crystals of palmkernel oil obtained by stirred crystallization in the presence of sucrose polylaurate.

At microscopic inspection (see FIG. 1B) the effect of the additive is that the crystals and crystal aggregates formed in the oil are conspicuously different from the crystals obtained without the crystallization modifying substance (FIG. 1B). Instead of brittle needle-like crystals, large and non-porous spherulites are formed. Since a stearin fraction with such crystals retains less of the olein fraction, even at low or moderate filtration pressure, the altered crystallization results in a considerable increase of the separation efficiency and facilitates stirred crystallization.

Although the invention is useful for solvent fractionation or detergent fractionation, the process is carried out preferably as a dry fractionation process.

The sucrose laurate is suitably applied in an amount of 0.005–2 wt. % on the total amount of oil. A useful amount is about 1 wt. %.

The invention is illustrated by the following examples:

EXAMPLES 1–2

Dry Fractionation of Palmkernel Oil

A sample was prepared containing 1000 g of palmkernel oil (neutralised, bleached, deodorised) and 10 g (1%) of sucrose polylaurate. The sample was heated and stirred at 65° C. until completely liquefied (no solid fat content) and then slowly cooled. Crystallization proceeded in a stagnant (0 rpm) mode at the chosen temperature of 23° C. until a constant solid phase content was reached. The sample was filtered and pressed at 12 bar for 30 minutes. After filtration and pressing, the solid phase content (SE=separation efficiency) of the cake was measured by NMR. For comparison the fractionation was repeated with the only difference that no sucrose polylaurate was added.

In example 2, palmkernel oil was fractionated following the same procedure as described above, but in a stirred mode (5 rpm).

Table I shows the results of these fractionations, together with the enhancement of the separation efficiency caused by the addition of the habit modifying substance.

EXAMPLES 3–9

Dry Fractionation of Lauric Oils

The dry fractionation process of example 2 is repeated with various lauric oils and two sucrose laurates. Each experiment has been carried out with and without crystal habit modifier. Table I indicates the SE and the relative improvements caused by the habit modifier.

The lauric oils are coconut oil (#3), an enzymatically interesterified mixture of 30 wt. % fractionated palmoil-stearin (POs) and 70 wt. % fractionated palmkernel-stearin: ei(30 POs/70 PKs) (#4), the same fat, only with a ratio 50/50 POs/PKs (#5), the same fat with a ratio 60/40 POs/PKs (#6), the chemically interesterified mixture of 60 wt. % hydrogenated palmoil (PO58) and 40 wt. % hydrogenated palmkernel (PK39): in (60PO58/40PK39) (#7) and the chemically interesterified mixture of 25 wt. % fully hydrogenated soybean oil (BO65) and 75 wt. % coconut oil (CN): in (25BO65/75CN) (#8).

Example 9 repeats example 5 but a sucrose polyester is used and which contains 75 wt. % esterified laurate and 25 wt. % esterified palmitate.

The results of Table I show that the addition of sucrose polylaurate to the fractionation of a lauric oil leads to a considerable increase of the separation efficiency.

TABLE I

| # | fat | CHM | rpm | c wt. % | SE wt. % | δ (%) |
|---|---|---|---|---|---|---|
| 1 | PK | sucrose polylaurate | 0 | 0.0<br>1.0 | 46<br>73 | +59 |
| 2 | PK | sucrose polylaurate | 5 | 0.0<br>1.0 | n.d.[1]<br>71 | ++ |
| 3 | CN | sucrose polylaurate | 5 | 0.0<br>1.0 | 28<br>48 | +71 |
| 4 | ei(30POs/70PKs) | sucrose polylaurate | 10 | 0.0<br>1.0 | 58<br>65 | +12 |
| 5 | ei(50POs/50PKs) | sucrose polylaurate | 10 | 0.0<br>1.0 | 63<br>75 | +19 |
| 6 | ei(60POs/40PKs) | sucrose polylaurate | 10 | 0.0<br>1.0 | 61<br>70 | +15 |
| 7 | in(60PO58/40PK39) | sucrose polylaurate | 32 | 0.0<br>1.0 | 63<br>68 | +8 |
| 8 | in(25BO65/75CN) | sucrose polylaurate | 10 | 0.0<br>1.0 | 49<br>54 | +10 |
| 9 | ei(50POs/50PKs) | sucrose polyester (75% laurate 25% palmitate) | 10 | 0.0<br>1.0 | 63<br>67 | +6% |

TABLE II

| | | Comparative examples | | | | |
|---|---|---|---|---|---|---|
| # | fat | CHM | rpm | c wt. % | SE wt. % | δ (%) |
| A | mfPOs | sucrose polylaurate | 40 | 0.0<br>1.0 | 68<br>68 | 0 |
| B | ei(40BO/ 60BO65) | sucrose polylaurate | 30 | 0.0<br>1.0 | 74<br>60 | −19 |
| C | ei(50POs/ 50PKs) | sucrose polystearate | 10 | 0.0<br>1.0 | 63<br>63 | 0 |
| D | ei(50POs/ 50PKs) | sucrose trilaurate | 10 | 0.0<br>1.0 | 63<br>54 | −14 |
| E | ei(50POs/ 50PKs) | inulin polylaurate | 10 | 0.0<br>0.1 | 63<br>49 | −22 |
| F | ei(50POs/ 50PKs) | sucrose polypalmitate | 10 | 0.0<br>1.0 | 63<br>54 | −14 |
| G | ei(50POs/ 59PKS) | sucrose polyester (25% laurate 35% palmitate 40% stearate) | 10 | 0.0<br>1.0 | 63<br>57 | −10 |

Tables I and II:

| | |
|---|---|
| c in wt. % | concentration of crystal habit modifier |
| rpm | stirrer rotation speed |
| SE in wt. % | separation efficiency |
| n.d. | not done, separation impossible |
| δ in % | enhancement SE relative to blank |

If not mentioned specifically, the esterification degree of sucrose-esters is 5–6.

Comparative Examples A–G

Example 2 is repeated but either with a non-lauric fat or with an additive different from the afore-defined sucrose laurate. The SE could not be improved and in most cases even was lowered.

The tried non-lauric oils are double stage dry fractionated palmoil stearin (mfPOs) (#A) and an enzymatically interesterified mixture of 40 wt. % soybean oil (BO) and 60 wt. % hydrogenated soybean oil (BO65), denoted as ei(40BO/60BO65) (#B).

The deviant additives are used with the enzymatically interesterified mixture of 50 wt. % fractionated palmoil stearin (POs) and 50 wt. % fractionated palmkernel stearin (PKs) of example 5. The additives are sucrose polystearate (#C), sucrose trilaurate (#D), which is a sucrose ester with a maximum esterification degree of 3, inulin polylaurate (#E), which is a polysaccharide ester of lauric acid, sucrose polypalmitate (#F) and a sucrose polyester (#G) which contains only 25 wt. % of laurate and further palmitate (35 wt. %) and stearate (40 wt. %). The fractionation results of these comparative examples are shown in Table II.

It appears that with non-lauric oils the separation efficiency cannot be improved when sucrose polylaurate is added. It also shows that no improved fractionation of lauric oils is obtained with a sucrose polyester other than the afore-defined sucrose polylaurate.

We claim:

1. A dry fractionation process for fractionating a lauric oil with improved separation of solid fatty material from partially crystallised lauric oil, which comprises the steps:

a. heating the oil until no longer a substantial amount of solid triglyceride is present in the oil, b. cooling and crystallising the triglyceride oil resulting in a solid stearin phase besides a liquid olein phase and c. recovering the stearin phase by separating it from the olein phase, where before crystallization starts a crystallization modifying substance is added to said triglyercide oil or to a solution of said triglyceride oil in an inert solvent, characterized in that the crystallization modifying substance is a sucrose laurate having an average esterification degree of 50–100% and a lauric acid content which is 40–100 wt. % of the total fatty acid content.

2. Process according to claim 1, characterised in that the sucrose laurate has a lauric acid content which is 60–100 wt. % of the total fatty acid content.

3. Process according to claims 1 or 2, characterised in that the sucrose laurate is used in an amount of 0.005–2 wt. % on the total amount of oil.

4. Process according to claim 1 characterised in that the crystallization proceeds in a stirred mode.

5. Process according to claim 1 characterised in that the lauric oil is a triglyceride oil or a mixture of triglyceride oils having a content of lauric acid which is 10–75 wt. % calculated on total fatty acid content.

6. Process according to claim 5, characterised in that the lauric oil is palmkernel oil or coconut oil.

7. A process according to claim 2 wherein the sucrose laurate has a lauric acid content of 75–100 wt. % of the total fatty acid content.

8. Process according to claim 5 wherein the lauric oil is a triglyceride oil or mixture of triglyceride oils having a content of lauric acid which is 30–60 wt. % calculated on total fatty acid content.

* * * * *